United States Patent
Geonnotti et al.

(10) Patent No.: US 11,351,103 B2
(45) Date of Patent: Jun. 7, 2022

(54) METHOD OF PROVIDING ORAL CARE BENEFITS

(71) Applicants: Johnson & Johnson Consumer Inc., Skillman, NJ (US); Fertin Pharma A/S, Vejle (DK)

(72) Inventors: Anthony R. Geonnotti, Princeton, NJ (US); Patricia L. Golas, North Brunswick, NJ (US); Helle Wittorff, Vejle Ost (DK); Heidi Ziegler Bruun, Vejle Ost (DK); Dorthe Shackinger Boesen, Vejle Ost (DK)

(73) Assignee: Johnson & Johnson Consumer Inc., Skillman, NJ (US)

( * ) Notice: Subject to any disclaimer, the term of this patent is extended or adjusted under 35 U.S.C. 154(b) by 61 days.

(21) Appl. No.: 15/783,151

(22) Filed: Oct. 13, 2017

(65) Prior Publication Data

US 2018/0140521 A1    May 24, 2018

Related U.S. Application Data

(63) Continuation-in-part of application No. 15/356,175, filed on Nov. 18, 2016, and a continuation-in-part of application No. PCT/DK2016/050377, filed on Nov. 18, 2016.

(51) Int. Cl.
| | |
|---|---|
| *A61K 8/60* | (2006.01) |
| *A61Q 11/00* | (2006.01) |
| *A61K 9/20* | (2006.01) |
| *A61K 8/02* | (2006.01) |
| *A61K 9/00* | (2006.01) |

(52) U.S. Cl.
CPC .............. *A61K 8/60* (2013.01); *A61K 9/2018* (2013.01); *A61Q 11/00* (2013.01); *A61K 8/022* (2013.01); *A61K 9/006* (2013.01); *A61K 9/0056* (2013.01); *A61K 2800/92* (2013.01)

(58) Field of Classification Search
None
See application file for complete search history.

(56) References Cited

U.S. PATENT DOCUMENTS

| | | | |
|---|---|---|---|
| 4,627,977 A | 12/1986 | Gaffar et al. | |
| 4,820,506 A | 4/1989 | Kleinberg et al. | |
| 5,874,068 A | 2/1999 | Engelman et al. | |
| 6,146,661 A | 11/2000 | Hoshino | |
| 8,435,542 B2 | 5/2013 | Manley et al. | |
| 8,658,139 B1* | 2/2014 | Cutler | A61K 47/02 424/401 |
| 2011/0123462 A1 | 5/2011 | Mordas et al. | |
| 2011/0250247 A1* | 10/2011 | Boghmans | A23P 10/28 424/401 |
| 2015/0101627 A1 | 4/2015 | Marshall et al. | |
| 2016/0145203 A1* | 5/2016 | Gambogi | C07C 279/12 424/54 |

FOREIGN PATENT DOCUMENTS

| | | |
|---|---|---|
| CN | 1620509 A | 5/2005 |
| CN | 1709229 A | 12/2005 |
| EP | 0913148 A1 | 5/1999 |
| EP | 0922464 A1 | 6/1999 |
| EP | 1369109 A1 | 12/2003 |
| JP | 2003-125706 A | 5/2003 |
| JP | 2007-501273 A | 1/2007 |
| JP | 2008-511671 A | 4/2008 |
| JP | 2014-196278 A | 10/2014 |
| KR | 2009/021584 A | 3/2009 |
| WO | WO 2004/047785 A1 | 6/2004 |
| WO | WO 2007/041367 A2 | 4/2007 |
| WO | WO 2009/007768 A1 | 1/2009 |
| WO | WO 2013/125350 A1 | 8/2013 |
| WO | WO 2015/158637 A1 | 10/2015 |
| WO | WO 2016/061486 A1 | 4/2016 |

OTHER PUBLICATIONS

Merriam-Webster, "Swish", available at https://www.merriam-webster.com/dictionary/swish, accessed Nov. 25, 2019.*
International Search Report; PCT/US2017/050342; dated Nov. 30, 2017.
Module: Academic Press Dictionary of Science and Technology; http://search.credoreference.com/content/entry/apdst/module/0; 1996.
International Search Report; PCT/US2017/056554; dated Nov. 30, 2017.

* cited by examiner

*Primary Examiner* — H. Sarah Park

(57) ABSTRACT

Provided are methods of providing at least one oral care benefit by introducing a tablet into the oral cavity to generate a fluid and forcing at least a portion of fluid generated around the oral cavity, for example, by swishing, rinsing, washing, etc., to provide an oral care benefit.

17 Claims, No Drawings

METHOD OF PROVIDING ORAL CARE BENEFITS

CROSS-REFERENCE TO RELATED APPLICATION

This application is a continuation-in-part, and claims the benefit, of U.S. application Ser. No. 15/356,175 filed Nov. 18, 2016 and also claims the benefit of International Patent Application No. PCT/DK2016/050377 filed Nov. 18, 2016.

FIELD OF THE INVENTION

The present invention relates to a method of providing one or more benefits to the oral cavity. More specifically, the invention relates to methods of providing a tablet suitable for generating a swishable amount of fluid in the oral cavity to provide one or more oral care benefits.

BACKGROUND OF THE INVENTION

In a more perfect world, people would thoroughly cleanse their mouths after each meal as part of their routine oral hygienic practices. Unfortunately, several factors conspire to prevent widespread compliance with this basic requirement of a good oral cleaning regimen.

Oral cleansing can be difficult or inconvenient at times, depending on the nature of the cleansing and the situation in which the cleansing must occur. Brushing, flossing, cleaning your tongue and gargling using a variety of devices and compositions well-suited for the privacy of one's home are common oral care practices. However, the devices and compositions used in oral cleansing practices are less convenient to use away from home, where bathroom facilities might be scarce, unavailable or unsanitary. For example, portable flossers can clean teeth on the go, but they are not discreet as well as not enjoyable to use, therefore consumers do not use them compliantly.

As brushing, flossing, cleaning your tongue and gargling in public are not considered to be socially acceptable behaviors in many, if not all cultures, a variety of less obtrusive oral cleansing products have been developed. These include breath-freshening gums and lozenges. Although gums and lozenges have been formulated to achieve a variety of beneficial effects, they are not always socially acceptable. For example, gum is expressly banned from certain institutions, such as schools as well as in certain countries. Gums and mints are used over extended periods of time, and they require an amount of sucking or chewing action on the part of the consumer, which can be distracting, tedious and undesirable.

Another portable oral cleansing product is a mouthspray. Like a mouthwash, a mouthspray can provide the consumer with a quick burst of strong breath-freshening action, which might be overwhelming in an extended-consumption product like gum or lozenges. On the other hand, mouthsprays are obtrusive. Spraying a mouthspray typically generates a noise, which undesirably draws the attention of the public to the consumer. Moreover, mouthsprays are typically packaged in relatively expensive and complex metal canisters, which can clog in use and are not environmentally friendly. Furthermore, misdirecting the spray not only wastes the product, but can result in irritated eyes, a sticky face and/or stained clothing.

It is therefore desired to provide methods of providing at least one oral care benefit in easy to use forms.

SUMMARY OF THE INVENTION

One aspect the present invention provides methods of providing at least one oral care benefit by introducing a tablet into the oral cavity to generate a fluid and forcing at least a portion of fluid generated around the oral cavity, for example, by swishing, rinsing, washing, etc., to provide an oral care benefit.

DETAILED DESCRIPTION OF THE INVENTION

The present methods allow for the use of a tablet to generate a fluid that can be moved throughout the oral cavity to provide a variety of oral care benefits, thus leveraging the advantages associated with a tablet, including portability, ease of dosing, stability, including active stability, shipping, processing benefits, and the like, while also providing the tactile/sensory and efficacy benefits associated with a fluid format, such as a mouthwash or mouth rinse. Applicants have discovered that the methods of the present invention can be used to generate significant fluid in the mouth, as compared to known uses of known tablets/solid delivery vehicles, that can be then moved throughout the mouth to provide one or more benefits including, mouth cleaning, including debris removal, germ kill, including anti-plaque, anti-gingivitis, and reduction in malodor, biofilm disruption, prevention of bacterial attachment, modification of oral microbial community structure, modification of the metabolic profile of oral microbes, antiviral activity, anti-inflammatory, pH balance, tooth whitening, stain prevention, anti-sensitivity, anti-caries, enamel strengthening, breath freshening, oral hydration/dry mouth relief, erosion repair and prevention, active delivery and retention, sensory enhancement, mouth feel alteration, pain relief, wound healing, other benefits to the teeth, mucosa, tongue, and combinations of two or more thereof.

In certain embodiments, the methods of the present invention provide a unique combination of sensory properties in addition to efficacy in providing oral care benefits including, for example, a desirable resistance to crunch, mouthfeel, watering effect, and combinations of two or more thereof. In certain embodiments, the methods include depositing the tablet in the mouth and chewing which includes a mechanical crunching/biting of the tablet. As discussed further below, in such embodiments, the tablets have a desirable "bite" or resistance to crunch. The mouthfeel provided in certain embodiments is preferably described as relatively smooth, that is, with a reduced sandy or gritty feeling, or a quick transition out of any sandy or gritting feeling while chewing or dissolving the tablet in the mouth. With respect to the watering effect, it is preferred to have a watering or salivation effect to facilitate mouthfeel benefits and/or generation of fluid.

The methods of the present invention provide for a surprising amount of generated fluid to be held and moved in the mouth for a period of time to allow for one or more oral care benefits. In certain embodiments, the methods of the present invention use tablets to generate a mass of fluid, recorded as the amount in grams at about 40 seconds ($G_{40}$) measured via the Fluid Generation Test described herein below, that is about 4 grams or more, including about 4.1 grams or more, about 4.2 grams or more, about 4.3 grams or more, about 4.4 grams or more, about 4.5 grams or more, about 4.6 grams or more, about 4.7 grams or more, about 4.8 grams or more, about 4.9 grams or more and about 5 grams or more. In certain preferred embodiments, the methods use tablet that have a $G_{40}$ of about 4.3 grams or more, including about 4.5 grams or more and about 4.8 grams or more. As shown in Example 2, by way of comparison, a variety of comparative tablets exhibited an $G_{40}$ of less than 4 grams, including less than 3.9 and less than 3.5 grams.

Any of a variety of tablets may be used in accord with the present invention to generate fluid. In certain preferred embodiments, the tablets of the present invention are chewable, dissolvable tablets. As will be recognized by those of skill in the art, chewable, dissolvable tablets include tablets that can be bitten and chewed by a user and tend to dissolve over time, as opposed to, for example, gums and/or relatively harder solid formats (e.g. lozenges and/or hard candies) which tend to be more difficult to bite (hard solid formats) and/or contain portions that do not dissolve over time for its normal use (gums). Accordingly, the tablets of the present invention tend to have a hardness that allows for biting and chewing the tablet by a user, including, for example, a hardness of 300 Newtons (N) or less as measured using the Tablet Hardness Test described herein. In certain embodiments, the tablets of the present invention have a hardness of from about 25 to about 250 N, including less than 200N, from about 25 to about 200N, from about 25 to about 160N, from about 25 to about 100N, and from about 100 to about 200N. In certain preferred embodiments, the tablets have a hardness of from about 25 to about 160N, including from about 25 to about 100N, and from about 25 to about 50N.

The tablets of the present invention may be of any suitable size/weight for use in generating a fluid for use in the methods. In certain embodiments, the tablets are greater than 1 gram, including about 1.1 grams or greater, about 1.2 grams or greater, about 1.3 grams or greater, or about 1.5 grams or greater. In certain preferred embodiments, the tablets are from about 1.1 grams to about 3 grams, including from about 1.1 grams to about 2.5 grams, from about 1.1 grams to about 2 grams, from about 1.3 grams to about 2.5 grams, from about 1.3 grams to about 2 grams, from about 1.5 grams to about 2.5 grams, and from about 1.5 grams to about 2 grams. In certain preferred embodiments, the tablets are from about 1.3 to about 2 grams, including from about 1.5 grams to about 2 grams.

In certain embodiments, the tablets of the present invention may be of any appropriate thickness, including a thickness of from about 5 to about 15 millimeters (mm), from about 5 to about 12 mm, from about 6 to about 12 mm, from about 8 to about 12 mm, from about 7 to about 8 mm. The tablets may also have a diameter, diagonal, or longest edge length of any suitable size including from about 5 to about 20 mm, from about 8 to about 18 mm, from about 10 to about 18 mm, from about 12 to about 18 mm, and from about 12 to about 16 mm.

The tablets of the present invention may be prepared via any of a variety of tableting methods known in the art. Conventional methods of tablet production include direct compression ("dry blending"), dry granulation followed by compression, wet granulation followed by drying and compression, application of energy to a blend of materials to be tableted, including applying heat, microwave, infrared, and other energies, combinations of two or more thereof, and the like. Each of these methods are described in detail in the art will be readily recognized by one of skill in the art. In certain preferred embodiments, the tablets are made via direct compression.

The tablets of the present invention may comprise any of a variety of materials suitable for use therein. In certain embodiments, the tablets of the present invention comprise at least one carbohydrate. Examples of carbohydrates include but are not limited to sugars such as dextrose, dextrose monohydrate, lactose, glucose, fructose, maltodextrin, sucrose, corn syrup solids and mannose; carbohydrate alcohols, such as sugar alcohols including sorbitol, lactitol, xylitol, erythritol, mannitol, maltitol, isomalt, and polyols; and combinations of two or more thereof. In certain preferred embodiments, the tablets comprise one or more sugar alcohols selected from the group consisting of xylitol, erythritol, maltitol, and isomalt, including, for example, xylitol, maltitol and combinations thereof, or xylitol, erythritol, isomalt and combinations thereof including combinations of xylitol, erythritol, and isomalt. In certain preferred embodiments, the tablets comprise erythritol alone or in combination with one or more additional sugar alcohols. In certain preferred embodiments, the tablets comprise xylitol alone or in combination with one or more additional sugar alcohols. In other preferred embodiments, the tablets comprise one or more sugar alcohols selected from the group consisting of sorbitol, lactitol, xylitol, mannitol, maltitol, isomalt, and combinations two or more thereof.

The carbohydrates for use in the present invention may be direct compressible (DC) or non-directly compressible (non-DC). The terms DC and non-DC are readily understood by one of skill in the art. Suppliers of sugar alcohols provide clear guidance to the user as for the ability for use in relation to compression of tablets. A non-DC particle in this connection is referred to as a particle which is not expressly recommended by the supplier for compression. An example of a non-DC grade of erythritol is Zerose™ erythritol 16952F supplied by Cargill whereas an example of a direct compressible (DC) grade of erythritol includes Zerose™ DC 16966 also supplied by Cargill. In certain embodiments, the tablets comprise both DC and non-DC carbohydrates. In certain embodiments, the tablets comprise non-DC erythritol in combination with one or more DC sugar alcohols. In other embodiments, the tablets comprise DC carbohydrates and are substantially free of non-DC sugar alcohols. As used herein throughout, the term "substantially free" means a weight percent amount based on the weight of the tablet that is 10% or less, preferably 5% or less, preferably 1% or less, preferably 0.5% or less, preferably 0.1% or less of the referenced substantially-free material. In certain embodiments, the term substantially-free means that the tablet is free (has 0%) of the referenced substantially-free material.

In certain embodiments comprising non-DC erythritol, the amount of non-DC erythritol particles is relatively high. It is particularly high when considering that the erythritol in a conventional sense is not regarded attractive for compression, but the mouthfeel and salivation perceived by the user in such methods is improved when compared to low amounts or the same amounts of DC erythritol.

In certain embodiments, the tablets of the present invention comprise a total amount of all carbohydrates in amount of at least 40% by weight of the tablet, including from about 40 to about 99%, from about 60 to 99%, from about 75 to about 95%, from about 80 to about 90% by weight of the tablets. In certain preferred embodiments, the carbohydrates comprise one or more sugar alcohols, and the tablet comprises a total amount of sugar alcohols of at least 40% by weight of the tablet, including from about 40 to about 99%, from about 60 to 99%, from about 75 to about 95%, from about 80 to about 90% by weight of the tablets. In certain embodiments, the tablets comprise at least 20% of each of two or more carbohydrates, including at least 20% of xylitol and at least 20% of one or more other sugar alcohols. In certain embodiments, the tablet comprises from about 20-50% of xylitol, including mixtures comprising from about 20-50% xylitol and from about 20-50% of erythritol (DC or non-DC), including from about 20-50% of xylitol, from about 20-40% of non-DC erythritol, and from about 20-40% of isomalt. In certain embodiments, the tablets comprise from about 20-50% xylitol and at least 20% of one other sugar alcohol selected from the group consisting of sorbitol, lactitol, mannitol, maltitol, isomalt, and combinations two or more thereof.

In certain embodiments, the tablets are sugar-free. As will be readily understood by one of skill in the art, such tablets may contain sugar alcohols but are nevertheless substantially free of sugars such as glucose, dextrose, sucrose, or oligomers/polymers of sugar molecules.

The tablets of the present invention may comprise one or more active ingredients for use in providing an oral care benefit. In certain embodiments, the active ingredients include, but are not limited to, any of a variety of actives for providing benefits such as mouth cleaning, including debris removal, antimicrobial, including anti-plaque, anti-gingivitis, and reduction in malodor, biofilm disruption, prevention of bacterial attachment, modification of oral microbial community structure, modification of the metabolic profile of oral microbes, antiviral activity, anti-inflammatory, pH balance, tooth whitening, stain prevention, anti-sensitivity, anti-caries, enamel strengthening, breath freshening, oral hydration/dry mouth relief, erosion repair and prevention, active delivery and retention, sensory enhancement, mouth feel alteration, pain relief, wound healing, and the like.

In certain embodiments, compositions of the present invention comprise essential oils. Essential oils are volatile aromatic oils which may be synthetic or may be derived from plants by distillation, expression or extraction, and which usually carry the odor or flavor of the plant from which they are obtained. Useful essential oils may provide antiseptic activity. Some of these essential oils also act as flavoring agents. Useful essential oils include but are not limited to citra, thymol, menthol, methyl salicylate (wintergreen oil), eucalyptol, carvacrol, camphor, anethole, carvone, eugenol, isoeugenol, limonene, osimen, n-decyl alcohol, citronel, a-salpineol, methyl acetate, citronellyl acetate, methyl eugenol, cineol, linalool, ethyl linalaol, safrola vanillin, spearmint oil, peppermint oil, lemon oil, orange oil, sage oil, rosemary oil, cinnamon oil, pimento oil, laurel oil, cedar leaf oil, gerianol, verbenone, anise oil, bay oil, benzaldehyde, bergamot oil, bitter almond, chlorothymol, cinnamic aldehyde, citronella oil, clove oil, coal tar, eucalyptus oil, guaiacol, tropolone derivatives such as hinokitiol, avender oil, mustard oil, phenol, phenyl salicylate, pine oil, pine needle oil, sassafras oil, spike lavender oil, storax, thyme oil, tolu balsam, terpentine oil, clove oil, and combinations thereof.

In certain preferred embodiments, the tablet of the present invention comprises one or more bioactive essential oils selected from the group consisting of menthol, thymol, eucalyptol, and methyl salicylate. In certain preferred embodiments, the tablet comprises menthol and at least one other essential oil selected from thymol, eucalyptol, and methyl salicylate. In certain preferred embodiments, the tablet comprises menthol and eucalyptol, menthol, eucalyptol and thymol, or menthol, eucalyptol, thymol, and methyl salicylate. Thymol, $[(CH_3)_2CHC_6H_3(CH_3)OH$, also known as isopropyl-m-cresol], is only slightly soluble in water but is soluble in alcohol, and its presence is one of the reasons alcohol was necessary in the well-established, high alcohol commercial mouth rinses. Methyl salicylate, $[C_6H_4OHCOOCH_3$, also known as wintergreen oil], additionally provides flavoring to the together with its antimicrobial function. Eucalyptol ($C_{10}H_{18}O$, also known as cineol) is a terpene ether and provides a cooling, spicy taste. Eucalyptol may be used in place of thymol in certain formulations in the same amount if desired. Menthol $(CH_3C_6H_9(C_3H_7)OH)$, also known as hexahydrothymol) is also only slightly soluble in alcohol, and is fairly volatile. Menthol, in addition to any antiseptic properties, provides a cooling, tingling sensation.

Other suitable antimicrobial agents include Halogenated Diphenyl Ethers, 2',4,4'-trichloro-2-hydroxy-diphenyl ether (Triclosan), 2,2'-dihydroxy-5,5'-dibromo-diphenyl ether, Halogenated Salicylanilides, 4'5-dibromosalicylanilide, 3,4', 5-trichlorosalcylanilide, 3,4',5-tribromosalicylanilide, 2,3,3', 5-tetrachlorosalicylanilide, 3,3',5-tetrachlorosalicylanilide, 3,5, dibromo-3'-trifluoromethyl salicylanilide, 5-n-octanoyl-3'-trifluoromethyl salicylanilide, 3,5-dibromo-4'-trifluoromethyl salicylanilide, 3,5-dibromo-3'-trifluoro methyl salicylanilide (Flurophene), Benzoic Esters, Methyl-p-Hydroxybenzoic Ester, Ethyl-p-Hydroxybenzoic Ester, Propyl-p-Hydroxybenzoic Ester, Butyl-p-Hydroxybenzoic Ester, Halogenated Carbanilides, 3,4,4'-trichlorocarbanilide, 3-trifluoromethyl-4,4'-dichlorocarbanilide 3,3',4-trichlorocarbanilide, Phenolic Compounds (including phenol and its homologs, mono- and poly-alkyl and aromatic halo (e.g. F, Cl, Br, I)-phenols, resorcinol and catechol and their derivatives and bisphenolic compounds), 2 Methyl-Phenol, 3 Methyl-Phenol, 4 Methyl-Phenol, 4 Ethyl-Phenol, 2,4-Dimethyl-Phenol, 2,5-Dimethyl-Phenol, 3,4-Dimethyl-Phenol, 2,6-Dimethyl-Phenol, 4-n-Propyl-Phenol, 4-n-Butyl-Phenol, 4-n-Amyl-Phenol, 4-tert-Amyl-Phenol, 4-n-Hexyl-Phenol, 4-n-Heptyl-Phenol, 2-Methoxy-4-(2-Propenyl)-Phenol (Eugenol), Mono- And Poly-Alkyl And Aralkyl Halophenols, Methyl-p-Chlorophenol, Ethyl-p-Chlorophenol, n-Propyl-p-Chlorophenol, n-Butyl-p-Chlorophenol, n-Amyl-p-Chlorophenol, sec-Amyl-p-Chlorophenol, n-Hexyl-p-Chlorophenol, Cyclohexyl-p-Chlorophenol, n-Heptyl-p-Chlorophenol, n-Octyl-p-Chlorophenol, O-Chlorophenol, Methyl-o-Chlorophenol, Ethyl-o-Chlorophenol, n-Propyl-o-Chlorophenol, n-Butyl-o-Chlorophenol, n-Amyl-o-Chlorophenol tert-Amyl-o-Chlorophenol, n-Hexyl-o-Chlorophenol, n-Heptyl-o-Chlorophenol, p-Chlorophenol, o-Benzyl-p-Chlorophenol, o-Benzyl-m-methyl-p-Chlorophenol o-Benzyl-m,m-dimethyl-p-Chlorophenol, o-Phenylethyl-p-Chlorophenol, o-Phenylethyl-m-methyl-p-Chlorophenol, 3-Methyl-p-Chlorophenol, 3,5-Dimethyl-p-Chlorophenol, 6-Ethyl-3-methyl-p-Chlorophenol, 6-n-Propyl-3-methyl-p-Chlorophenol, 6-iso-Propyl-3-methyl-p-Chlorophenol, 2-Ethyl-3,5-dimethyl-p-Chlorophenol, 6-sec Butyl-3-methyl-p-Chlorophenol, 2-iso-Propyl-3,5-dimethyl-p-Chlorophenol, 6-Diethylmethyl-3-methyl-p-Chlorophenol, 6-iso-Propyl-2-ethyl-3-methyl-p-Chlorophenol, 2-sec Amyl-3,5-dimethyl-p-Chlorophenol, 2-Diethylmethyl-3,5-dimethyl-p-Chlorophenol, 6-sec Octyl-3-methyl-p-Chlorophenol, p-Bromophenol, Methyl-p-Bromophenol, Ethyl-p-Bromophenol, n-Propyl-p-Bromophenol, n-Butyl-p-Bromophenol, n-Amyl-p-Bromophenol, sec-Amyl-p-Bromophenol, n-Hexyl-p-Bromophenol, cyclohexyl-p-Bromophenol, o-Bromophenol, tert-Amyl-o-Bromophenol, n-Hexyl-o-Bromophenol, n-Propyl-m,m-Dimethyl-o-Bromophenol, 2-Phenyl Phenol, 4-chloro, 2-methyl phenol, 4-chloro-3-methyl phenol, 4-chloro-3,5-dimethyl phenol, 2,4-dichloro-3,5-dimethylphenol, 3,4,5,6-terabromo-2-methylphenol, 5-methyl-2-pentylphenol, 4-isopropyl-3-methylphenol, 5-chloro-2-hydroxydiphenylemthane, Resorcinol And Its Derivatives, Resorcinol, Methyl-Resorcinol, Ethyl-Resorcinol, n-Propyl-Resorcinol, n-Butyl-Resorcinol, n-Amyl-Resorcinol, n-Hexyl-Resorcinol, n-Heptyl-Resorcinol, n-Octyl-Resorcinol, n-Nonyl-Resorcinol, Phenyl-Resorcinol, Benzyl-Resorcinol, Phenylethyl-Resorcinol, Phenylpropyl-Resorcinol, p-Chlorobenzyl-Resorcinol, 5-Chloro-2,4-Dihydroxydiphenyl Methane, 4'-Chloro-2,4-Dihydroxydiphenyl Methane, 5-Bromo-2,4-Dihydroxydiphenyl Methane, 4'-Bromo-2,4-Dihydroxydiphenyl Methane, Bisphenolic Compounds, Bisphenol A, 2,2'-methylene bis(4-chlorophenol), 2,2'-methylene bis(3,4,6-trichlorophenol) (hexachlorophene), 2,2'-methylene bis(4-chloro-6-bromophenol), bis(2-hydroxy-3,5-dichlorophenyl) sulfide, bis(2-hydroxy-5-chlorobenzyl) sulfide, menthoxy-1,2-propanediol, ortho-methoxy cinnamic aldehyde, menthyl-3-hydroxybutanoate, combinations of two or more thereof, and the like.

Other antimicrobial agents include, but are not limited to: hexetidine; fatty acid compounds such as caproic acid, caprilic acid, capric acid, lauric acid, myristic acid, myristoleic acid, palmitic acid, palmitoleic acid, stearic acid, oleic acid, elaidic acid, linoleic acid, linolenic acid, linolelaidic acid, arachidonic acid vitamin E, vitamin E acetate, apigenin and mixtures thereof; long chain fatty alcohols such as described in US Patent publication US 20110123462 to Mordas et al., herein incorporated by reference in its entirety, (examples of which include, but are not limited to 1-decen-3-ol; cis-4-decen-1-ol, trans-2-decen-1-ol, cis-2-nonen-1-ol, cis-4-decenal, trans-2-decenal, cis-7-decenal, cis-5-octen-1-ol, trans-2-octen-1-ol, 1-octen-3-ol, cis-3-nonen-1-ol, trans-2-nonen-1-ol, cis-6-nonen-1-ol, 9-decen-1-ol, trans-2-undecen-1-ol, trans-2-dodecen-1-ol, trans-2-octenal, trans-2-nonenal, 6-nonenal, cis-2-decenal, trans-2-undecenal, trans-2-dodecenal, cis-3-octen-1-ol, 3-octen-2-ol, 10-undecen-1-ol, trans-2-tridecen-1-ol, stereoisomers thereof and mixtures thereof); cyclic sesquiterpene alcohols, such as farnesol; N'-alkyl-L-arginine alkyl ester (e.g., Lauroyl Arginine Ethyl Ester) and salts such as described in U.S. Pat. No. 5,874,068 to Engelman et al., herein incorporated by reference in its entirety; Amino acid derivative compounds as described in U.S. Patent Publication No. 20160145203 to Gambogi, et al., herein incorporated by reference in its entirety; antimicrobial peptides, such as retrocyclin (RC101), protegrin-1 (PG1) or KSL-W; and surfactants, including cationic surfactants such as cetylpyridinium chloride, chlorhexedine and mixtures thereof. Additionally, antimicrobial extracts of certain botanical or fruits may be included, including proanthocyanidins (PACs) found in cranberry such as, flavan-3-ols (and polymers of), procyanidins (and polymers of), terpenes (and polymers of), hydroxybenzole acids, hydroxycinnamic acids, anthocyanidins (and polymers of), flavonols (and polymers of), and other cyanidins and peonidins. Oils such as peppermint oil and sage oil are also useful herein.

Other suitable actives include fluoride ion sources such as sodium fluoride, sodium monofluorophosphate, stannous fluoride, and amine fluorides (providing, for example, about 1-5000 ppm of fluoride ion, optionally about 200-1150 ppm of fluoride ion); non-fluoride tooth strengthening agents such as calcium carbonate, alpha tricalcium phosphate, or phosphoryl oligosaccharides of calcium, anticalculus agents, such as water-soluble pyrophosphate salts, preferably alkali metal pyrophosphates, polyacrylates and copolymers of maleic anhydride or acid and methyl vinyl ether (e.g., Gantrez), as described, for example, in U.S. Pat. No. 4,627,977, to Gaffar et al; as well as, e.g., polyamino propane sulfonic acid (AMPS), zinc citrate trihydrate, polypeptides (such as polyaspartic and polyglutamic acids), and mixtures of two or more thereof; anti-calculus agents such as water-soluble pyrophosphate salts, preferably alkali metal pyrophosphates; chelating agents such as tartaric acid and pharmaceutically-acceptable salts thereof, citric acid and alkali metal citrates and mixtures thereof; tooth desensitization agents which reduce tooth sensitivity including potassium salts such as potassium nitrate and potassium chloride and strontium salts such as strontium chloride and strontium acetate; tooth whitening agents and vitamins such as vitamin A; as well as pigments and colorants such as inorganic white pigments, inorganic colored pigments, pearling agents, filler powders and the like, as well as talc, mica, magnesium carbonate, calcium carbonate, magnesium silicate, aluminum magnesium silicate, silica, titanium dioxide, zinc oxide, red iron oxide, brown iron oxide, yellow iron oxide, black iron oxide, ferric ammonium ferrocyanide, manganese violet, ultramarine, nylon powder, polyethylene powder, methacrylate powder, polystyrene powder, silk powder, crystalline cellulose, starch, titanated mica, iron oxide titanated mica, bismuth oxychloride, and mixtures of two or more thereof.

Enzymes are another type of active that may be used in the present compositions. Useful enzymes include those that belong to the category of proteases, lytic enzymes, plaque matrix inhibitors and oxidases: Proteases include papain, pepsin, trypsin, ficin, bromelin; cell wall lytic enzymes include lysozyme; plaque matrix inhibitors include dextranases, mutanases; and oxidases include glucose oxidase, lactate oxidase, galactose oxidase, uric acid oxidase, peroxidases including horse radish peroxidase, myeloperoxidase, lactoperoxidase, chloroperoxidase. The oxidases also have whitening/cleaning activity, in addition to antimicrobial properties.

Ingredients which are metabolized by oral bacteria to cause a benefit effect in the oral cavity may also be included in these tablets, including arginine, arginine monohydrochloride, and inulin-type fructans, maltodextrin, fructooligosaccharides and galactooligosaccharides. Additionally, these tablets may be used to deliver probiotic strains of bacteria, including certain species of lactobacilli and bifidobacteria, *Saccharomyces* spp, streptococci, enterococci and commensal *Escherichia coli*.

The tablet may also be used to deliver pharmaceutical actives to treat oral diseases or disease symptoms which occur in the oral cavity or the oropharynx, such as anesthetics, antibiotics, antifungals, antiviral, and anti-inflammatory compounds.

In certain embodiments, the tablets for use in the present invention may comprise any of a variety of salivation agents (also known as salivary stimulants or salivary agents). Suitable salivation agents include food organic acids such as citric, lactic, malic, succinic, ascorbic, adipic, fumaric, tartaric acids, parasympathomimetic drugs, such as choline esters like pilocarpine hydrochloride, or cholinesterase inhibitors, and combinations of two or more thereof. Additional suitable salivary stimulants are described, for example, in U.S. Pat. Nos. 4,820,506 and 8,435,542 which are incorporated herein in their entirety. In certain preferred embodiments, the salivation agents comprise citric acid, succinic acid, or a combination thereof alone or in combination with other salivation agents. In certain preferred embodiments, the salivation agent comprises jambu oleoresin extract as described in U.S. Pat. No. 8,435,542. The salivation agent may be present in any suitable amount for use in the present invention including, from about 0.001 to about 5% by weight of the tablet, including from about 0.01 to about 3%, from about 0.01 to about 1% from about 0.01 to about 0.5%, from about 0.01 to about 0.25%, and from about 0.01 to about 0.1% by weight of the tablet.

The tablets for use in the present invention may comprise any of a variety of additional ingredients suitable for use in the tablets including, for example, sweeteners, lubricants, fillers, adsorbents, disintegrants, glidants, superdisintegrants, flavor and aroma agents, antioxidants, preservatives, texture enhancers, coloring agents, and the like, and mixtures of two or more thereof.

In certain embodiments, the tablets may comprise additional sweeteners including, but not limited to, synthetic or natural sugars; artificial sweeteners such as saccharin and its salts including sodium saccharin, aspartame, acesulfame and its salts including potassium acesulfame, thaumatin, glycyrrhizin, sucralose, dihydrochalcones, alitame, miraculin, monellin, stevioside, and combinations of two or more thereof. In certain preferred embodiments, the tablets comprise sucralose, potassium acesulfame, or a combination thereof. The tablets may comprise any suitable total amounts of additional sweeteners including from 0.001 to about 8% by weight, including from about 0.02 to about 8%, from about 0.1 to about 3%, from about 0.1 to about 1%, and from about 0.1 to about 0.5% by weight of the tablet.

The tablets may also include lubricant materials in certain embodiments. Suitable lubricants include, but are not limited to, long chain fatty acids and their salts, such as magnesium stearate and stearic acid, talc, glycerides waxes, and mixtures thereof. Such materials may be present in any suitable amount including from about 0.01 to about 5%, including from about 0.1 to about 5%, from about 0.5 to about 3%, including from about 0.5 to about 2% by weight of the tablet.

Suitable fillers include, but are not limited to, water insoluble plastically deforming materials (e.g., microcrystalline cellulose or other cellulosic derivatives), and mixtures thereof. Suitable adsorbents include, but are not limited to, water-insoluble adsorbents such as dicalcium phosphate, tricalcium phosphate, silicified microcrystalline cellulose (e.g., such as distributed under the PROSOLV brand (PenWest Pharmaceuticals, Patterson, N.Y.)), magnesium aluminometasilicate (e.g., such as distributed under the NEUSILIN brand (Fuji Chemical Industries (USA) Inc., Robbinsville, N.J.)), clays, silicas, bentonite, zeolites, magnesium silicates, hydrotalcite, veegum, and mixtures thereof. Suitable disintegrants include, but are not limited to, sodium starch glycolate, cross-linked polyvinylpyrrolidone, cross-linked carboxymethylcellulose, starches, microcrystalline cellulose, and mixtures thereof.

Examples of superdisintegrants include, but are not limited to, croscarmellose sodium, sodium starch glycolate and cross-linked povidone (crospovidone). In one embodiment, the tablet contains up to about 5% by weight of such superdisintegrant.

Examples of flavors and aromatics include, but are not limited to, essential oils including distillations, solvent extractions, or cold expressions of chopped flowers, leaves, peel or pulped whole fruit containing mixtures of alcohols, esters, aldehydes and lactones; essences including either diluted solutions of essential oils, or mixtures of synthetic chemicals blended to match the natural flavor of the fruit (e.g., strawberry, raspberry and black currant); artificial and natural flavors of brews and liquors, e.g., cognac, whisky, rum, gin, sherry, port, and wine; tobacco, coffee, tea, cocoa, and mint; fruit juices including expelled juice from washed, scrubbed fruits such as lemon, orange, and lime; spear mint, pepper mint, wintergreen, cinnamon, cacoe/cocoa, vanilla, liquorice, menthol, eucalyptus, aniseeds nuts (e.g., peanuts, coconuts, hazelnuts, chestnuts, walnuts, colanuts), almonds, raisins; and powder, flour, or vegetable material parts including ginger.

Examples of antioxidants include, but are not limited to, tocopherols, ascorbic acid, sodium pyrosulfite, butylhydroxytoluene, butylated hydroxyanisole, edetic acid, and edetate salts, and mixtures thereof.

Examples of preservatives include, but are not limited to, citric acid, tartaric acid, lactic acid, malic acid, acetic acid, benzoic acid, and sorbic acid, and mixtures thereof.

Examples of texture enhancers include, but are not limited to, pectin, polyethylene oxide, and carrageenan, and mixtures thereof. In one embodiment, texture enhancers are used at levels of from about 0.1% to about 10% percent by weight.

In one embodiment, the tablets further contain one or more effervescent couples. In one embodiment, effervescent couple contains one member from the group consisting of sodium bicarbonate, potassium bicarbonate, calcium carbonate, magnesium carbonate, and sodium carbonate, and one member selected from the group consisting of citric acid, malic acid, fumaric acid, tartaric acid, phosphoric acid, and alginic acid. In one embodiment, the combined amount of the effervescent couple(s) in the powder blend/tablet is from about 2 to about 20 percent by weight, such as from about 2 to about 10 percent by weight of the total weight of the powder blend/tablet.

In some embodiments, the tablets may be made by mixing its ingredients and heating them until they melt into a syrup, then exposing the mixture to pressurized carbon dioxide gas (about 600 pounds per square inch, or psi) and allowing it to cool. The process causes tiny high-pressure bubbles to be trapped inside the candy. When the tablet is placed in the mouth and comes into contact with saliva, the tablet breaks and dissolves, releasing the carbon dioxide from the bubbles, resulting in a popping and sizzling sound and leaving a slight tingling sensation.

As noted above, in preferred embodiments, the tablets of the present invention are not gums and are substantially free of gum bases as used conventionally to manufacture gums, as opposed to chewable, dissolvable tablets. In preferred embodiments, the tablets of the present invention are not sufficiently heated to form hard candies nor lozenges as such terms and their manufacture is understood in the art and which product forms are intended to dissolve more slowly than chewable, dissolvable tablets.

The methods of the present invention comprise introducing into the oral cavity a tablet of the present invention. Any of a variety of know means may be used in the introducing step. For example, a tablet may be placed by hand into a user's mouth, the tablet may be introduced via an applicator, packaging, container, dosing apparatus, or other article or machine suitable for such purpose.

The methods of the present invention further comprise generating a fluid in the oral cavity after introducing the tablet, preferably a fluid comprising ingredients from the tablet introduced into the oral cavity. As will be readily understood, in preferred embodiments, the step of generating a fluid includes stimulating the production of saliva in the oral cavity either alone or in combination with other means for generating fluid. Preferably, the step of generating a fluid includes dissolving at least a portion of the tablet and stimulating the production of saliva in any order either sequentially and/or simultaneously. In preferred embodiments, the fluid is generated in accord with the present invention without introducing additional fluid, e.g. water, solvent, or other beverage or ingestible fluid into the oral cavity with the tablet. In preferred embodiments, the tablet is not mixed with water/fluid prior to or contemporaneously with introducing the tablet into the oral cavity, nor is additional water/fluid added to the tablet in the oral cavity to generate the fluid in accord with the present invention.

In certain embodiments, after introducing a tablet, the methods of the present invention comprise chewing said tablet to generate a fluid in the oral cavity, preferably chewing said tablet to dissolve, or while dissolving, at least a portion thereof and generate a fluid comprising ingredients from said tablet. The tablet may be chewed for any time sufficient to generate fluid in accord with embodiments comprising a chewing step, including, for example, chewing for at least 5 seconds, including at least 10 seconds, at least 15 seconds, at least 20 seconds, or at least 30 seconds. In certain preferred embodiments, the tablet is chewed for about 10 seconds or for at least 10 seconds.

The present methods comprise the step of forcing at least a portion of fluid generated around the oral cavity. As used herein, the forcing step comprises applying any suitable amount of force within the oral cavity to move fluid in any one or more directions, e.g., from side to side, up, down, back, forth, forward, back, around, onto and/or through teeth, gums, cheek, and/or another surface in the oral cavity. In certain embodiments, the fluid is forced (a) from a lingual surface of the oral cavity toward or onto a buccal and/or labial surface of the oral cavity, (b) from a buccal and/or labial surface of the oral cavity toward or onto a lingual surface of the oral cavity, or both (a) and (b). In certain embodiments, the fluid is forced around the oral cavity using muscular movements of the cheeks and/or tongue. In certain embodiments, the fluid is forced around the oral cavity with the lips closed. In certain preferred embodiments, the forcing step comprises forcing at least a portion of the fluid generated around the mouth, with lips closed, using muscular movements of the cheeks and tongue. The fluid may be forced in any suitable manner in accord with the present invention, including, for example, by swishing, rinsing, washing, swirling, gargling, agitating, threshing, sloshing, irrigating, actuating, gushing, douching, swooshing, splooshing, squooshing, pushing, maneuvering, mixing, twisting, flowing, bathing, circulating, distributing, dispersing, wetting, moving, and the like, the fluid in any one or more directions, or otherwise using the fluid as a mouthwash, mouth rinse, or other liquid oral care product. The fluid may be forced/moved within the oral cavity for any suitable period of time including at for at least 5 seconds, including at least 10 seconds, at least 15 seconds, at least 20 seconds, or at least 30 seconds. In certain preferred embodiments, the fluid is agitated for about 30 seconds or for at least 30 seconds.

In certain embodiments, the fluid generated in the present methods may be swallowed/ingested by a user or may be expelled/spit out after the moving step. In certain preferred embodiments, the methods comprise swallowing at least a portion of the fluid.

Without intending to be limiting, an example of one embodiment of a present method in use may include (a) introducing a tablet into the oral cavity of a user, in general said tablet being suitable to generate fluid and/or preferably having an $G_{40}$ of at least 4 grams, (b) having the user chew the tablet to generate a fluid, preferably for a suitable amount of time to generate fluid, which fluid preferably contains materials/ingredients from the tablet which have been introduced therein via the chewing and/or dissolving of at least a portion of the tablet; and (c) swishing, or otherwise moving, at least a portion of the fluid in the mouth prior to (d) swallowing. In another embodiment, a user may introduce a tablet into the oral cavity and allow the tablet to dissolve to generate fluid at least a portion of which is then moved in the oral cavity and then swallowed or expectorated.

In certain preferred embodiments, the methods of the present invention comprise methods of cleaning the mouth. Such methods may include methods of removing debris from the oral cavity, including, for example, removing food particles or other debris within the teeth or gums and/or providing breath freshening and killing of germs associated with bad breath. Applicants have recognized that the present methods allow for sufficient fluid generation from a tablet, as compared to prior art tablets, that can be moved throughout the mouth to remove debris in an effective manner and/or deliver antimicrobial actives from the tablet to the surfaces of the oral cavity to kill germs. In other preferred embodiments, the methods of the present invention comprise methods of killing germs associated with bad breath, plaque and/or gingivitis by introducing a tablet of the present invention comprising at least one antimicrobial active.

EXAMPLES

Example 1

Tablets

Tablets E1-E4 and C1-C3 were made using the ingredients listed in Table 1. All ingredients were received in powder form. The ingredients were blended together into a powder blend and compressed using either a SMI P2007-212b 6-ton single station tablet press (Tablets E1, E2, C1, C2) or a Fette 3090i.

TABLE 1

| | Tablet Formula | | | | | | |
|---|---|---|---|---|---|---|---|
| | E1 | E2 | E3 | E4 | C1 | C2 | C3 |
| Weight (grams) | 1.5 g | 1.5 g | 1.6 g | 1.2 g | 1 g | 1 g | 1 g |
| Ingredients (wt %) | | | | | | | |
| Xylitol | 20 | 20 | 38.94 | 38.94 | 20 | 20 | 20 |
| Non-DC Erythritol | | | 27.5 | 27.5 | | | |
| Isomalt | | | 20.11 | 20.11 | | | |
| Maltitol | 72.73 | 77.8 | | | 72.73 | 77.8 | 73.8 |
| Calcium Carbonate | | | 7 | 7 | | | |
| Sucralose | 0.15 | 0.15 | 0.16 | 0.16 | 0.15 | 0.15 | 0.15 |
| Potassium Acesulfame | 0.05 | 0.05 | 0.055 | 0.055 | 0.05 | 0.05 | 0.05 |
| Color | | | 0.169 | 0.169 | | | |
| Magnesium Stearate | 2 | 2 | 1 | 1 | 2 | 2 | 2 |
| Salivary Agent[1] | 0.07 | | 0.07 | 0.07 | 0.07 | | |
| Flavor[2] | 5 | 5 | 5 | 5 | | | |
| Flavor | | | | | | | 4 |

[1]Comprises jambu oleoresin extract.
[2]Comprises menthol, eucalyptol, eugenol, menthoxy-1,2-propanediol, ortho-methoxy cinnamic aldehyde, menthyl-3-hydroxyutanoate, and other flavor ingredients.

Example 2

Fluid Generation

The fluid generation properties of the tablets were measured in accord with the Fluid Generation Test below to determine the amount in grams of fluid generated after 40 seconds ($G_{40}$) wherein the 40 seconds includes chewing for 10 seconds and swishing/moving the fluid for 30 seconds. The $G_{40}$ associated with tablets E1-E4 and C1-C3 made in accord with Example 1 were measured. Also measured were Altoids® brand peppermints (C4) available commercially from Wrigley's having a list of ingredients including sugar, gum arabic, artificial flavors, gelatin, and color (Red 40), and an average weight measured to be about 0.72 grams.

Fluid Generation Test

Participants were provided with a tablet and instructed to chew the tablet for 10 seconds, then move the fluid generated around their mouth (swish) for 30 seconds, then spit into pre-weighed cup. Final mass of generated fluid spit into the cup after 40 seconds was determined: (final cup mass with saliva)−(empty cup mass) in grams. The overall average of mass of at least 8 (N) participants was reported as the $G_{40}$ associated with the tablets as listed in Table 2 below. Note: SEM=standard error of the mean.

TABLE 2

| Fluid Generation | | | | | | | |
|---|---|---|---|---|---|---|---|
| | C1 | E1 | C2 | E2 | E3 | C4 | E4 |
| Average ($G_{40}$) | 3.88 | 4.72 | 3.94 | 4.37 | 5.09 | 3.24 | 4.33 |
| SEM | 0.22 | 0.25 | 0.22 | 0.28 | 0.26 | 0.23 | 0.31 |
| N | 12 | 13 | 13 | 10 | 12 | 9 | 9 |

The Fluid Generation properties of tablets were also measured via paired comparison with other tablets by the same participant as shown in Tables 3 and 4 (each participant is compared to themselves). The reported data in Table 3 is the difference in grams of fluid generated by the first listed tablet minus the amount generated by the second listed tablet. The data reported in Table 4 is the percentage change of fluid generated by the first listed tablet as compared to the second listed tablet.

TABLE 3

| Paired Comparison of Fluid Generation (Mass) | | | | | | | |
|---|---|---|---|---|---|---|---|
| | E1 vs C1 | E2 vs C2 | C1 vs C2 | E1 vs E2 | E3 vs E1 | E3 vs C4 | E4 vs C1 |
| Average | 0.89 | 0.59 | 0.08 | 0.33 | 0.33 | 1.76 | 0.48 |
| SEM | 0.19 | 0.23 | 0.13 | 0.21 | 0.11 | 0.19 | 0.23 |
| N | 12 | 10 | 11 | 10 | 12 | 9 | 9 |
| 95% CI | 0.37 | 0.46 | 0.26 | 0.42 | 0.21 | 0.38 | 0.45 |
| P < 0.05 | Yes | Yes | No | No | Yes | Yes | Yes |
| P < 0.1 | Yes | Yes | No | Yes | Yes | Yes | Yes |

TABLE 4

| Paired Comparison of Fluid Generation (Percentage) | | | | | | | |
|---|---|---|---|---|---|---|---|
| | E1 vs C1 | E2 vs C2 | C1 vs C2 | E1 vs E2 | E3 vs E1 | E3 vs C4 | E4 vs C1 |
| Average | 24% | 19% | 3% | 9% | 8% | 57% | 14% |
| SEM | 5% | 8% | 4% | 6% | 3% | 8% | 6% |
| Count | 12 | 10 | 11 | 10 | 12 | 9 | 9 |
| 95% CI | 9% | 16% | 7% | 11% | 5% | 15% | 12% |
| P < 0.05 | Yes | Yes | No | No | Yes | Yes | Yes |
| P < 0.1 | Yes | Yes | No | Yes | Yes | Yes | Yes |

Example 3

Germ Kill

The germ kill properties associated with the tablets were measured in accord with the following procedure:

Materials
Prereduced 9 ml 0.1% Peptone tubes
Prereduced 4.95 ml PO4 tubes
Sterile 18 mm glass test tubes with caps
Sterile 3 mm Glass Beads
Sakura Test Sample Tablets
Human Saliva
Sterile Stainless Steel Spatula
Prereduced 1.9 ml Autoclaved DiH2O Tubes
Prereduced OOPS Agar Plates Germ Kill Measurement Method The day before the test, pre-reduce all tubes and plates in an anaerobic chamber Preparation of Saliva inoculum
Pool and homogenize saliva from a minimum of 6 donors.
Create a 50% saliva solution by adding 25 mls of prereduced 0.1% peptone to 25 mls of saliva Crush 1 sample tablet with a clean mortar and pestle (clean with 70% IPA and wipe with Kim Wipe) and place into an 18 mm test tube with 6 sterile 3 mm glass beads.

Add 4 ml of prepared, prewarmed diluted saliva inoculum to the test tube with the crushed tablet (reaction tube) and begin timer To test water, as the negative control, place 1.9 ml into the test tube and add 4 mls of prepared, prewarmed diluted saliva and vortex.

Vortex the reaction tube for a total of 35 or 45 seconds.

After the 35 or 45 second exposure time, take 50 μL of reaction mixture from the reaction tube and dispense into 4.95 mL of neutralizing broth and vortex for 5 seconds These will be referred to as $10^{-2}$ dilutions.

Dilute and plate on OOPS III agar.

After 5 days at 35° C. anaerobic incubation, dark colonies (VSC-producing organisms) were enumerated on OOPs III and compared to the sterile water controls. Percent reductions compared to water treatment were calculated.
Results are shown in Table 5.

TABLE 5

| | Germ Kill | | | | | |
|---|---|---|---|---|---|---|
| Name | Water Control | C1 | E1 | C2 | E2 | E3 |
| CFU/ml | 1.29E+07 | 1.66E+06 | 4.37E+05 | 1.34E+07 | 1.22E+07 | 2.17E+06 |
| Percent reduction compared to water control | n/a | 87% | 97% | −4% | 5% | 83% |

Example 4

Tablet Hardness

The hardness of tablets was measured by a PharmaTest_PTB311E according to instrument instructions (the Tablet Hardness test). The results are shown in Table 6 below. Note: SEM=standard error of the mean.

TABLE 6

| | Tablet Hardness | | | | | |
|---|---|---|---|---|---|---|
| | Formula | | | | | |
| | C1 | C2 | E1 | E2 | E3 | C4 |
| Thickness (mm) | 7.50 | 7.78 | 10.91 | 11.11 | 7.48 | 6.11 |
| Diameter/width (mm) | 12.79 | 12.70 | 12.74 | 12.68 | 13.65 | 12.71 |
| Average Hardness (in Newtons) | 34.09 | 34.93 | 30.89 | 28.54 | 145.87 | 220.93 |
| SEM | 0.45 | 0.25 | 0.54 | 0.89 | 2.95 | 6.68 |
| N | 10 | 10 | 10 | 7 | 10 | 4 |

Example 5

Debris Removal

The ability/efficacy of removing debris in accord with the present methods was tested as described below.
Debris Removal Test:
Determination of Baseline Amount of Cracker Residue Left After Chewing:

Participants were instructed to chew a Saltine™ cracker for 30 seconds and swallow. Immediately after swallowing, participants swished with 10 ml of water for 30 second and spit their mouth contents into a Millipore Steriflip® Sterile 50 ml Disposable Vacuum filtration system with a 100-micron nylon net filter (Catalog number SCNY00100). Vacuum was applied for approx. 10 second until all water was removed. Any excess liquid was blotted away from the rim of the filter. The filter with cracker residue was then weighed and the difference between the weight of the filter+cracker residue and the average weight of an unused clean filter (N=11) was calculated. This mass was used as the baseline amount of cracker left in a participant's mouth after eating a cracker.
Determination of the Amount of Cracker Residue Removed by Tablet Use As before, participants were instructed to chew a Saltine™ cracker for 30 seconds and swallow. Immediately after swallowing, participants were instructed to place a tablet E3 in their mouth, chew for 10 seconds, swish the liquid for 30 seconds, then swallow. Immediately after swallowing, participants swished with 10 ml of water for 30 seconds and spit their mouth contents into a Millipore Steriflip® Sterile 50 ml Disposable Vacuum filtration system with a 100-micron nylon net filter (Catalog number SCNY00100). Vacuum was applied for approx. 10 second until all water was removed. Any excess liquid was blotted away from the rim of the filter. The filter with cracker residue was then weighed and the difference between the weight of the filter+cracker residue and the average weight of an unused clean filter (N=11) was calculated. This mass was used as the amount of cracker left in a participant's mouth after chewing a cracker and using a tablet to clean their mouth and remove debris. The results are shown in Table 7.

TABLE 7

| | Debris Removal | | |
|---|---|---|---|
| Participant | Cracker residue baseline (grams) | Cracker reside after tablet E3 use (grams) | Percent reduction in residue (Baseline-Tablet)/Baseline * 100 |
| 1 | 0.8341 | 0.2915 | 65.05% |
| 2 | 0.3396 | 0.234 | 31.10% |
| 3 | 0.3295 | 0.1175 | 64.34% |
| 4 | 0.3875 | 0.2998 | 22.63% |
| 5 | 0.7535 | 0.4275 | 43.26% |
| | AVERAGE | | 45.28% |

Example 6

Consumer Testing

Applicants have evaluated the consumer experience in using the tablets as a solid form that can be chewed and generate fluid to be used, e.g. as a mouthwash or rinse. The tablets of the present invention provide suitability as a chewable tablet and desirable watering effect to produce sufficient fluid for swishing.

The rating of consumer experience of the present methods compared to other methods was tested. The results are shown in Table 8.

TABLE 8

| % of participants reporting (N = 96) | C3 | E3 |
|---|---|---|
| Too little liquid* | 38% | 19% |

TABLE 8-continued

| % of participants reporting (N = 96) | C3 | E3 |
|---|---|---|
| Liked the experience of chewing and swishing the product* | 46% | 61% |

*Significant at a 90% level

What is claimed is:

1. A method of providing at least one oral care benefit comprising:
   i. introducing a tablet into the oral cavity;
   ii. chewing the tablet;
   iii. generating a swishable amount of fluid in the oral cavity by chewing the tablet without introducing additional fluid into the oral cavity with the tablet;
   iv. forcing at least a portion of the fluid generated in step iii back and forth through teeth and around the oral cavity;
   v. removing debris from the oral cavity and delivering antimicrobial actives by the forcing of the fluid in step iv; and
   vi. swallowing or expelling said portion of fluid after forcing the fluid in step iv;
   wherein said tablet has a $G_{40}$ of about 4.3 grams or more;
   wherein said tablet comprises from about 40% to about 99% by weight of the tablet of one or more sugar alcohols selected from the group consisting of sorbitol, lactitol, xylitol, erythritol, mannitol, maltitol, isomalt, and combinations of two or more thereof; and
   wherein said tablet comprises a salivary agent.

2. The method of claim 1 wherein said tablet is greater than 1 gram.

3. The method of claim 2 wherein said tablet is about 1.2 grams or greater.

4. The method of claim 1 wherein said tablet has a hardness of less than 200N.

5. The method of claim 1 wherein said tablet has a hardness of from about 25 to about 160N.

6. The method of claim 1 wherein said tablet comprises at least 20% by weight of xylitol.

7. The method of claim 1 wherein said tablet comprises xylitol, erythritol, and isomalt.

8. The method of claim 7 wherein said erythritol comprises non-directly compressible erythritol.

9. The method of claim 1 wherein said tablet is essentially free of non-directly compressible erythritol.

10. The method of claim 1 wherein said tablet comprises at least one essential oil selected from the group consisting of menthol, thymol, eucalyptol, methyl salicylate and combinations of two or more thereof.

11. The method of claim 1 wherein said forcing step comprises forcing the fluid around the oral cavity for at least 30 seconds.

12. A method of cleaning the oral cavity comprising:
   a. introducing into said oral cavity a tablet comprising a salivary agent and from about 40 to about 99% by weight of sugar alcohols selected from the group consisting of sorbitol, lactitol, xylitol, erythritol, mannitol, maltitol, isomalt, and combinations of two or more thereof, said tablet having a weight of about 1.3 to about 2 grams;
   b. chewing the tablet;
   c. generating a swishable amount of fluid in the oral cavity by chewing the tablet without introducing additional fluid into the oral cavity with the tablet;
   d. forcing the generated fluid of step c back and forth through teeth and around the oral cavity;
   e. removing debris from the oral cavity and delivering antimicrobial actives by forcing of the fluid in step d; and
   f. swallowing at least a portion of said generated fluid; and
   wherein said tablet has a $G_{40}$ of about 4.3 grams or more.

13. The method of claim 12 wherein said tablet has a hardness of from about 25 to about 160N.

14. The method of claim 13 wherein said tablet further comprises one or more antimicrobial essential oils.

15. The method of claim 14 wherein said method comprises killing germs associated with bad breath, plaque, gingivitis, or combinations of two or more thereof.

16. The method of claim 15 wherein said one or more antimicrobial essential oils comprises menthol, thymol, eucalyptol, methyl salicylate, or a combination of two or more thereof.

17. The method of claim 16 wherein said forcing step comprises forcing said fluid for at least 30 seconds prior to swallowing.

* * * * *